United States Patent [19]

Tu et al.

[11] Patent Number: 5,061,276
[45] Date of Patent: Oct. 29, 1991

[54] MULTI-LAYERED POLY(TETRAFLUOROETHYLENE)/ELASTOMER MATERIALS USEFUL FOR IN VIVO IMPLANTATION

[75] Inventors: Roger Tu, Lake Forrest; Edwin Wang, Irvine, both of Calif.

[73] Assignee: Baxter International Inc., Deerfield, Ill.

[21] Appl. No.: 286,440

[22] Filed: Dec. 19, 1988

Related U.S. Application Data

[63] Continuation-in-part of Ser. No. 43,326, Apr. 28, 1987, Pat. No. 4,816,339.

[51] Int. Cl.⁵ ............................................... A61F 2/06
[52] U.S. Cl. ........................................ 623/1; 623/1
[58] Field of Search ................ 623/1, 12; 128/334 R; 606/151

[56] References Cited

U.S. PATENT DOCUMENTS

| | | |
|---|---|---|
| 3,479,670 | 11/1969 | Medell ................................. 623/1 |
| 4,193,138 | 3/1980 | Okita . |
| 4,229,838 | 10/1980 | Mano . |
| 4,286,341 | 9/1981 | Greer et al. . |
| 4,306,318 | 12/1981 | Mano et al. . |
| 4,321,711 | 3/1982 | Mano . |
| 4,482,516 | 11/1984 | Bowman et al. . |
| 4,550,447 | 11/1985 | Seiler Jr. et al. . |
| 4,576,608 | 3/1986 | Homsy . |
| 4,718,907 | 1/1988 | Karwoski et al. . |

Primary Examiner—Randall L. Green
Assistant Examiner—Gina Gualtieri
Attorney, Agent, or Firm—Michael C. Schiffer; W. Dennis Drehkoff

[57] ABSTRACT

A vascular graft having a composite structure prepared by wrapping about the external surface of a tube having one or more layers of polytetrafluoroethylene or a polytetrafluoroethylene-elastomeric polymer blend, either alone or in combination, an elastic fiber, while maintaining the fiber under tension. The elastic fibers can be wound about the entire length of the tube while being maintained under the same of different degrees of tension. Furthermore, the elastic fibers may be wound about the tube under a higher degree of tension along locations adjacent the opposite ends the tubing.

6 Claims, 7 Drawing Sheets

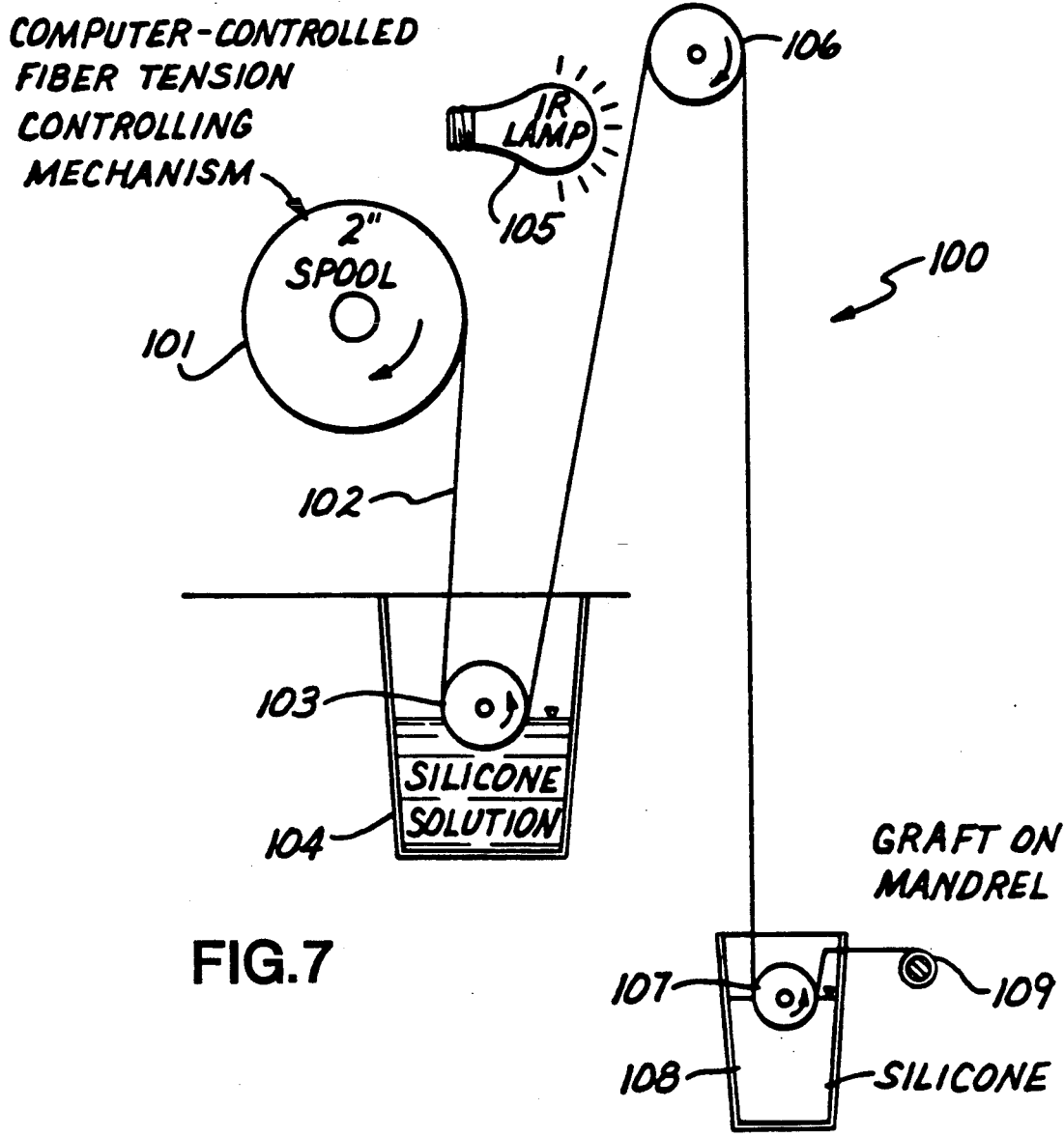
FIG.7
FIG.8
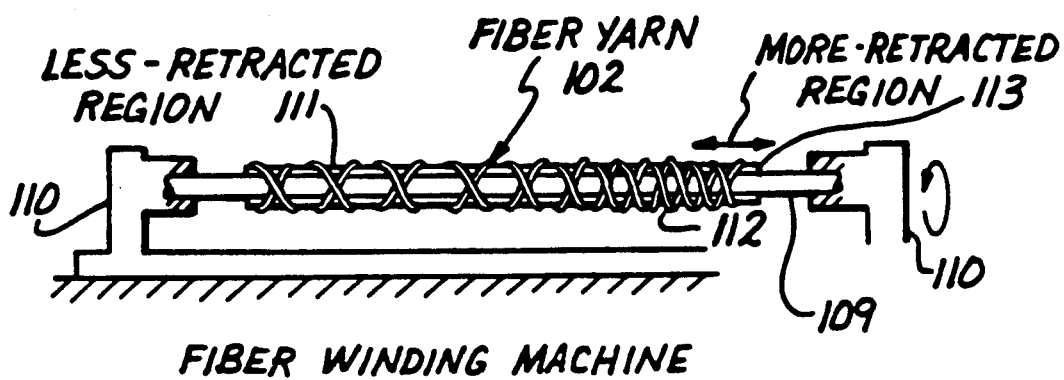
FIBER WINDING MACHINE

MULTI-LAYERED POLY(TETRAFLUOROETHYLENE)/ELASTOMER MATERIALS USEFUL FOR IN VIVO IMPLANTATION

RELATED PATENT APPLICATIONS

This is a continuation-in-part of U.S. patent application Ser. No. 043,326, filed on Apr. 28, 1987, now U.S. Pat. No. 4,816,339.

BACKGROUND OF THE INVENTION

Co-pending application Ser. No. 892,271 entitled "POROUS HIGHLY EXPANDED FLUOROPOLYMERS AND PROCESS THEREFOR", incorporated herein by reference, discloses the use of elastomers which strengthen expanded poly(tetrafluoroethylene) fibrils by forming a continuous matrix interpenetrating the microstructure of the fibrils. In so doing, it renders the poly(tetrafluoroethylene) structure porous but yet durable with excellent pliability for use as a vascular graft. More importantly, however, addition of an elastomer to the poly(tetrafluoroethylene) allows an implant or preferably, a vascular graft/made from the material to be biologically compatible with surrounding tissue.

This invention relates to a multi-layered polytetrafluoroethylene/elastomer composite structure that can be formed into an implant where there is an improvement in the luminal hydrophobicity, suturability, compliance, strength and elasticity due to the novel arrangement of respective layers of poly(tetrafluoroethylene), polytetrafluoroethylene/elastomer and elastomer. This invention relates to a composite structures, more specifically composite medical devices for in vivo implantation, such as heart valve leaflets, sutures, vascular access devices or any related products, but more particularly relates to vascular grafts.

Conventional vascular grafts manufactured from porous poly(tetrafluoroethylene) have limitations in their strength and compliance. The porous grafts do not hold or resist dilation unless reinforced in some manner. For example, vascular grafts have been reinforced by incorporating in the tube wall external ribs, see U.S. Pat. No. 4,550,447, issued to Seiler, Jr. et al on Nov. 5, 1985. Other methods of reinforcing vascular grafts include wrapping the vascular graft with a reinforcing film for support. This reinforcement slows down the tissue ingrowth preventing rapid healing. This is because of the relatively low radial tensile strength of poly(tetrafluoroethylene). In addition, the grafts are stiff and non-compliant to the natural artery.

Laminated vascular grafts have also been proposed with the laminated materials bonded in a manner to place porous, compacted poly(tetrafluoroethylene) in a position to be in contact with the blood surrounded by a layer of a suitable biocompatible material so that the implant allegedly may be accepted by the surrounding tissue. U.S. Pat. No. 4,576,608 describes a vascular graft having two layers, an inner layer comprising a blend of poly(tetrafluoroethylene) fibers and resin having a specific porosity wherein the outer layer comprises a fused blend of poly(tetrafluoroethylene) fibers and carbon fibers or silicone rubber. Other suitable biocompatible materials used in the lamination may be Teflon FEP, manufactured by DuPont Company or other biocompatible fabrics such as polyamide, polyaramid, polyimide or polyester fabric.

In U.S. Pat. No. 4,286,341, issued to Greer et al on Sept. 1, 1981, a vascular graft is disclosed which is formed from a substantially non-thrombogenic hydrogel, with the luminal surface having relatively small pores or microvoids suitable for tissue ingrowth, while the outer surface has a heterogenous microstructure including relatively large pores or macrovoids especially suitable for cellular ingrowth.

U.S. Pat. No. 4,321,711 discloses a vascular prosthesis comprising porous tubing of poly(tetrafluoroethylene) containing an anti-coagulant substance and bonded to its outside surface, a porous elastomer coating containing a substance which counteracts the anti-coagulant. Typically, the anti-coagulant substance is heparin. Any heparin antagonist such as protamine may be used in the elastomer coating to counteract the heparin. The elastomer is typically fluorine rubber, silicone rubber, etc. While the implants taught in the above discussed references may be porous and flexible, they do not provide the strength, elasticity or biological compatibility of the natural artery.

Other types of reinforced vascular grafts are taught in U.S. Pat. Nos. 4,193,138, issued to Okita on March 18, 1980., and 4,229,838, issued to Mano on Oct. 28, 1980. The vascular graft taught in Okita is a composite structure of a porous polytetrafluoroethylene tube in which the pores have been filled in with at least one water-insolubilized water-soluble polymer. Mano also teaches a composite vascular graft structure including a porous polytetrafluoroethylene tubing with a polyethyleneimine in the pores.

In U.S. Patent No. 4,718,907, issued to Karwoski et al on Jan. 12, 1988 a process is disclosed for depositing a fluorine-containing coating is disclosed. The process obtains the fluorine-containing coating by passing a polymerizable fluorine-containing gas through a tubular substrate, while a radio frequency field is being applied to cause the deposition and polymerization of the fluorine-containing gas on to the exposed surfaces of the substrate. The resulting product may be useful for preparing a vascular graft.

A process for preparing high strength porous polytetrafluoroethylene products is disclosed in U.S. Pat. No. 4,482,516, issued to Bowman et al on Nov. 13, 1984. The disclosed process involves densifying a polytetrafluoroethylene material to achieve the higher strength.

While the above described vascular grafts, or processes of preparing the same, provide for a stronger graft, such grafts do not possess the desired porosity necessary to achieve the requisite tissue ingrowth.

Another suggested approach for reinforcing vascular grafts is disclosed in U.S. Pat. No. 4,306,318, issued to Mano et al on Dec. 22, 1981. The disclosed vascular graft is prepared by helically wrapping an elastic fiber about the exterior surface of a porous tubing of polytetrafluoroethylene. The elastic fibers are wrapped about the exterior of the tubing and the adhered thereto. The strength imparted to the resulting vascular graft is dependent upon the tensile strength of the elastic fibers being used. This reinforcement is constant across the vascular graft.

There is a need for an in vivo implantable medical device, and in particular vascular grafts which are formed as a composite structure that mimics the natural artery composition of collagen and elastin and is acceptable to the surrounding tissue.

SUMMARY OF THE INVENTION

The present invention overcomes the disadvantages discussed above by providing for an implantable composite structure having increased elasticity, while remaining sufficiently porous to allow for tissue ingrowth.

The implantable composite structure of the invention is formed with one or more layers of polytetrafluoroethylene and/or a polyfluoroethylene-elastomer blend, and a layer of an elastomer, with the elastomer being in the form of a coating or fiber. The elastomer useful for preparing the polytetrafluoroethylene-elastomer blend may be selected from the group consisting of polyvinylidene fluoride co-hexafluoropropylene, poly(tetrafluoroethylene-co-perfluoro(methylvinylether)), poly(tetrafluoroethylene-co-propylene), poly(vinylidene-co-chlorotrifluorethylene), silicones, fluorosilicones, fluoroalkoxy phosphazenes, segmented copolyester ether, styrene butadiene block copolymers, polyethers, acrylonitrile butadienes, isoprenes, polyurethanes, and mixtures thereof. The elastomeric polymer coating or fiber may be selected from the same group of elastomers, and also silicone rubbers, fluorine rubbers, acrylic rubbers, natural rubbers or other biocompatable rubbers.

The composite structure may be in the shape of any suitable medical implantable device. However, the composite structure of the invention is particularly advantageous when in the form of a vascular graft.

One embodiment of the present invention includes in vivo implantable composite structures formed with a luminal layer of polytetrafluoroethylene and a second outer layer of the polytetrafluoroethylene-elastomer blend previously. Another composite structure of the present invention includes the above described luminal and second layers, and an outer fourth layer of an elastomeric polymer coating composite. A still further embodiment includes all three described four layers with a further outer layer of wound elastomeric polymer fibers previouslydescribed.

According to a preferred embodiment of the invention a vascular graft is in the form of a composite structure prepared by wrapping about the external surface of a tube having one or more layers of polytetrafluoroethylene or polytetrafluoroethylene, either alone or in combination, an elastic fiber, while maintaining the fiber under tension. The elastic fibers can be wound about the entire length of the tube while being maintained under the same or different degrees of tension. Furthermore, the elastic fibers may be wound about the tube under a higher degree of tension along locations adjacent the opposite ends the tubing.

The multi-layered composite structures of the present invention have excellent compliance, strength and elasticity because of the arrangement of the layers of poly(tetrafluoroethylene), poly(tetrafluoroethylene)/elastomer, elastomeric polymer coating or elastomeric polymer fibers.

DESCRIPTION OF THE DRAWINGS

The present invention may be better understood and the advantages will become apparent to those skilled in the art by reference to the accompanying drawings, wherein like reference numerals refer to like elements in the several figures, and wherein:

FIG. 7 is a schematic illustration of a preferred process of the invention;

FIG. 8 is a schematic illustration of the winding procedure of the preferred embodiment illustrated in FIG. 7.

DETAILED DESCRIPTION OF THE INVENTION

Figure 1:
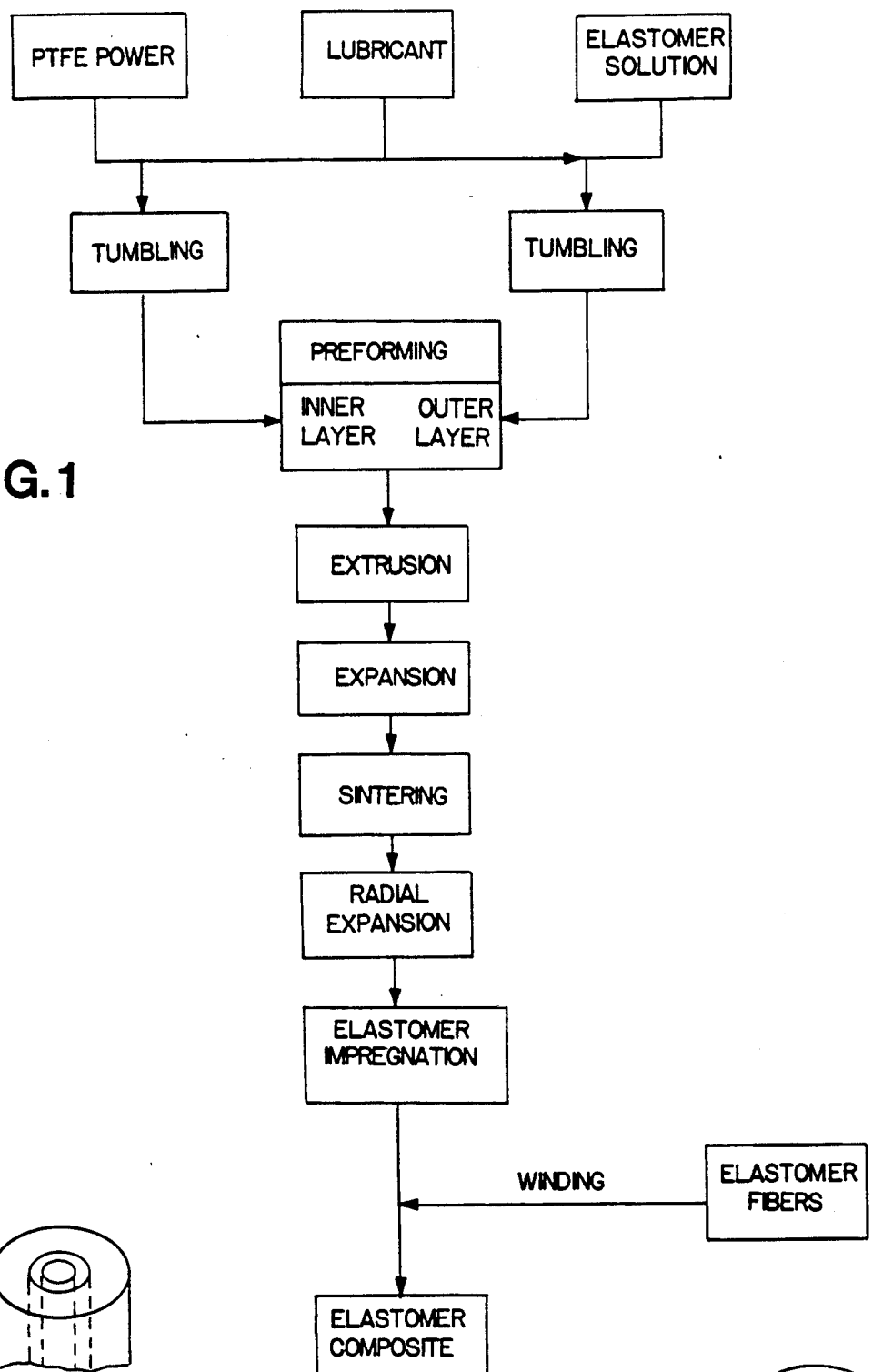
FIG. 1 is a schematic representation of a generalized process of making the implants of the present invention including various different interchangeable steps for different embodiments.

The composite structures of the present invention provides an improvement in luminal hydrophobicity, suturability, compliance, strength and elasticity. The use of poly(tetrafluoroethylene) as the luminal, or inner layer provides the resulting composite with a hydrophobic, blood compatible fibril-nodal microstructure. While the present invention will be described generally in relation to a composite structure, which may include various types of implantable medical devices, the present invention is particularly applicable for use in constructing vascular grafts.

The layer of the mixture of poly(tetrafluoroethylene) and elastomer, provides a porous composite matrix as a transitional phase between the inner poly(tetrafluoroethylene) layer and, if present, the outer elastomer layer. The poly(tetrafluoroethylene)-elastomer blend is less hydrophobic than straight poly(tetrafluoroethylene), which when used as the second layer provides a more compatibility with the in vivo environment, and provides a surface to which other composite structures, e.g. the elastomeric polymer coating or fibers may be bound.

For the purpose of describing the present invention the terms "elastomer" and "elastomeric polymer" shall mean any polymeric material which when in the form of a flat sheet or fiber can be stretched beyond twice its original dimension, and when released will return with force to substantially its original dimension.

The use of the optional layer of elastomeric polymer coating provides a hydrophilic tissue-compatible porous layer which promotes the elasticity, strength and suturability for the whole composite. The coating is prepared by mixing the elastomer with a conventional solvent such as 1,1,1-trichloroethane, tetrahydrofuran or Freon, depending on the specific elastomer. The solvent penetrates the pores of the second layer and evaporates to allow the pore shape size to remain relatively intact.

A preferred embodiment comprises an additional fourth layer of a polymeric elastomeric polymer fiber or fibers wrapped onto the outer elastomeric polymer coating. The outer elastomer layer of spirally bound fibers forms a non-woven matrix with large pore sizes which provides an excellent site for periprosthetic tissue anchoring. This is in contrast to the outer surface of the luminal layer of poly(tetrafluoroethylene) which does not promote tissue ingrowth and has little bonding strength.

In a still further preferred embodiment of the invention, an elastomeric polymer fiber is wrapped onto the outer surface of the composite substrate under tension. This embodiment is particularly useful in the preparation of vascular grafts. That is, the composite structure is a tubular shaped structure. The tubular shaped structure need not include an outer coating of an elastomer, and for that matter may include a single layer of a polytetrafluoroethylene or polytetrafluoroethylene-elastomer blend, with the more preferred embodiment being a composite structure having a luminal polytetrafluoroethylene layer and an outer polytetrafluoroethylene-elastomer blend layer. As will be described more fully herein, the composite structure becomes retracted by wrapping of the fiber under tension onto the outer surface of the structure. That is, as the fiber is being wrapped onto the surface the structure retracts or is compressed in both a radial and longitudinal direction. This retraction provides the substrate with an inherent elasticity, particularly when the substrate is pulled upon. This is particularly important when the substrate is a vascular graft. As blood flows through the graft the inherent elasticity provided by the fibers applied under tension minimizes the dilation of the graft.

Vascular grafts with intrinsic elasticity also self seal around any puncture holes providing during the surgical implantation. That is, the intrinsic elasticity of the material forming the vascular graft will retract about the puncture hole to essentially close this hole. This benefit is particular advantageous at the anastomosis site, that is, the site of attachment to a natural vascular structure. This ability to "self-seal" minimizes bleeding. Furthermore, the vascular grafts inherent elasticity reduces the potential of the graft tearing about the suture points. That is, the normal pulsating of the implanted vascular graft will exert a tension on the sutures. If the graft did not possess any elasticity, this applied tension would cause a rupturing of the graft about the suture in the long term.

A vascular graft formed from the multi-layered composite structure of the invention mimics the natural artery composition of collagen, which is needed for strength, and the natural artery composition of elastin, which is needed for elasticity. Vascular grafts prepared from the composite structure of the invention undergo endotheliazation rapidly as a result of enhanced tissue ingrowth.

The elastomers used to prepare the polytetrafluoroethylene-elastomer blend, and also for use as the coating may be selected from the group consisting of polyvinylidene fluoride co-hexafluoropropylene, poly(tetrafluoroethylene-co-perfluoro(methylvinylether)), poly(tetrafluoroethylene-co-propylene), poly(vinylidene-co-chlorotrifluoroethylene), silicones, fluorosilicones, fluoroalkoxy phosphazenes, segmented copolyester ether, styrene butadiene block copolymers, polyethers, acrylonitrile butadienes, isoprenes, polyurethanes, and mixtures thereof. The elastomer may be added to poly(tetrafluoroethylene) to form the polytetrafluoroethylene-elastomer blend in an amount which is effective to produce a medical implant having the desired properties of elasticity, porosity and biocompatibility. The amount of the elastomer applied to the outer surface of the composite is also in an amount effective to produce a medical implant with the desired properties. Preferably, these amounts range from about 5% by weight to about 120% by weight of the poly(tetrafluoroethylene) used in preparing the composite. Still more preferably, the amount of the elastomer used in preparing the polytetrafluoroethylene-elastomer blend is about 50% by weight of the poly(tetrafluoroethylene), while the amount of the elastomer used to form the outer coating is about 25% by weight of the poly(tetrafluoroethylene).

As stated, in accordance with a preferred embodiment elastomeric polymer fibers are wound onto the outer layer, which could be the elastomeric polymer coating or the poly(tetrafluoroethylene)-elastomer blend layer. The compliance of the composite structure is increased by the use of the elastomer in the polytetrafluoroethylene-elastomer blend, as the outer coating and as the fibers wrapped about the composite structure. This compliance provides for excellent hydrophilicity for improved tissue compatibility in the outer layers of the composite structure while the luminal layer, which is the polytetrafluoroethylene, has the required hydrophobicity to be compatible with blood.

While any of the aforementioned elastomers function in this invention, preferred elastomers are silicone or a co-polymer of propylene and tetrafluoroethylene, poly(tetrafluoroethylene-co-propylene), sold under the trade name Aflas manufactured by Asahi Glass Company. The structure of the preferred co-polymer, in which the tetrafluoroethylene and propylene arrange alternately in an orderly manner, is shown:

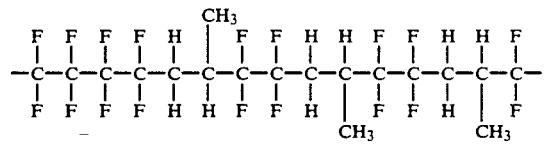

The composite structure of the invention may be prepared by paste forming the polytetrafluoroethylene and the polytetrafluoroethylene-elastomer blend, forming the paste into a preform which is extruded into layers in a shape of the final desired medical product. i.e. a tubular vascular graft. This formed structure is dried, with the optional elastic polymer coating and/or elastic fiber layer being applied at this time, the elastomeric polymer coating being applied by spraying or dipping to impregnate the outer polytetrafluoroethylene-elastomer blend layer. Finally, the composite structure is stretched to form a final expanded composite structure having the desired porosity.

The porous structure of the polytetrafluoroethylene-elastomer blend layer of the composite structure of this invention is composed of fine poly(tetrafluoroethylene) fibrils coated with the elastomer. The elastomer encapsulates and reinforces the poly(tetrafluoroethylene) fibrils. The elastomer is a continuous matrix interpenetrating the microstructure of the fibrils. It modifies the sharp edges of the fibrils and nodes to render the edges smooth. The smooth edges of the fibrils and nodes create a poly(tetrafluoroethylene) elastomer product resistant to suture tearing with high intrinsic elasticity. The pores are not individual, discrete openings. They are interconnected within the fibrils to provide for high porosity and relatively large pore size.

The asymmetric pore size differs with the individual layers. For example, the internodal distance of the pores of the luminal layer of poly(tetrafluoroethylene) is about 20 to 30 microns. The internodal distance of the pores of the polytetrafluoroethylene-elastomer blend layer may range from about 30 to about 500 microns, preferably about 50 to 100 microns. The pore size is ideal for fibroblast tissue ingrowth. The optional layer comprising the elastomeric polymer coating generally retains the pore size and porosity of the polytetrafluoroethylene-elastomer blend layer. The pores of optional elastic fiber layer would have an internodal distance of about 100 to about 2000 microns, preferably about 200 to about 500 microns.

The porosity of the entire composite structure can range from about 30% to 90%, preferably about 50% to about 90%. The large pore size of the outer layers, and in particular the large pore size of the elastic fiber layer, provide an excellent substrate for periprosthetic tissue anchoring. The porosity of the various layers of the implantable composite structure is achieved by the stretching of the composite structure at an expansion ratio of about 50 to about 500%, preferably 250% during preparation.

A multi-layered matrix of the composite structure of the invention may be obtained by producing a luminal layer of poly(tetrafluoroethylene) from poly(tetrafluoroethylene) powder and a second layer comprising lubricated poly(tetrafluoroethylene) powder admixed with an elastomer dispersion. Both the poly(tetrafluoroethylene) powder for the luminal layer and the poly(tetrafluoroethylene)/elastomer mixture are preformed.

The elastomer dispersion used in preparing the polytetrafluoroethylene-elastomer blend should contain about 2 to about 10% by weight of the elastomer. This dispersion is mixed with the lubricated poly(tetrafluoroethylene) powder. Preferably, about 5% by weight of the elastomer dispersion is utilized to provide a mixture with poly(tetrafluoroethylene) and lubricant so that the elastomer is present in an amount equal to about 10% by weight of the final polytetrafluoroethylene-elastomer blend on a solid basis. The amounts of each of the poly(tetrafluoroethylene) and elastomer needed to form the polytetrafluoroethylene-elastomer blend may be varied so that the elastomer may be present in amounts ranging from about 5% to about 60% by weight of the finished product. For a more detailed description of the process of preparing the polytetrafluoroethylene-elastomer blend, and the useful weight percentages of both the elastomer and the polytetrafluoroethylene used to prepare such blends, see U.S. patent application Ser. No. 043,326, filed on Apr. 28, 1987, with the relevant portions of such application being incorporated herein by reference.

Both the poly(tetrafluoroethylene) powder and the polytetrafluoroethylene-elastomer blend may be compressed to form a pre-form or billet which is extruded under conditions of elevated temperature and pressure to form the desired shape, e.g. a tubular form for a vascular graft. Alternately, the powder may be molded or rolled to form the desired shape. The resulting formed shape may then be cut, with the cut extrudate being heated to a temperature between 35° C. and the crystalline melting point of polytetrafluoroethylene, that is 327° C., or the decomposition of the elastomeric polymer, whichever is lower. Typically, the expansion temperature is below the melting point of polytetrafluoroethylene, or both about 300° C. Next, the formed shape is expanded either radially or longitudinally.

Expansion of the extrudate is accomplished biaxially or uniaxially. Uniaxial expansion rearranges the polytetrafluoroethylene matrix to elongate the nodes, with the longer axis of a node being oriented perpendicular to the direction of expansion. The fibrils in the polytetrafluoroethylene matrix become oriented parallel to the direction of expansion. The rate of stretch may vary and is not intended to be limiting. Preferably, the rate of stretch is 10% per second, however, it may range from 5% per second to about 100% per second. The composite structures can be expanded up to about 150 to about 600%, preferably about 350% of the original size in order to retain the excellent pore size and porosity previously described. The polytetrafluoroethylene and poly(tetrafluoroethylene)/elastomer layers can be stretched while retaining their desired functionality when heated to 35° C. to 327° C., preferably about 300° C. If the composite structure is a tubing for use as a vascular graft, then such tubing may be radially expanded by the means shown in co-pending application Serial No. 935,237, with those portions relating to the manner of stretching the tubing to form the vascular graft being incorporated herein by reference. The radial expansion of the inside diameter of the tubing may increase from about 5% to about 50%, preferably about 10 to about 50%. For example, if the inside diameter of the inner layer is 4 mm, it may be increased to 6 mm.

After the composite structure has been expanded it is sintered by insertion into an oven at temperatures ranging from 342° C. to 390° C. for a short period of time. Again, the methods for sintering polytetrafluoroethylene and polytetrafluoroethylene-elastomer blends are known, with such a method being described more fully in the incorporated herein reference.

If the composite structure is a vascular graft tubing it may be placed in a bath of an elastomer solution containing from about 2% to about 10% by weight elastomer after the expansion and sintering step. The bathing of the formed composite structure forms the desired outer elastomeric polymer coating. Alternatively, the elastomer may be sprayed on the expanded composite structure, i.e. tubing. Typically, from about 2% to about 25% by weight elastomer is added to the composite structure at this time. The elastomer solution should contain a solvent such as 1,1,1-trichloroethane or tetrahydrofuran, in an amount effective to allow the elastomer to coat and penetrate the pores of the polytetrafluoroethylene-elastomer blend layer.

If desired the elastic fibers are applied to the outer surface of the composite structure. i.e. the polytetrafluoroethylene or polytetrafluoroethylene-elastomer blend layer or the elastomeric polymer coating. These elastic fibers may be applied by any suitable manner. For example, if the composite structure is in the form of a vascular graft tubing, the tubing may be loaded on a mandril. Elastomeric polymer fibers are wound and bonded onto the outer layer of the porous tubing.

The fibers may be hydrophobic or hydrophilic. Hydrophobicity is conveniently refined as the % water absorption in 24 hours according to Americal Standards Testing Method D-570. The % water absorption should be less than 0.01. Examples of hydrophobic fibers, include but should not be limited to the following: silicones, butyl rubber, fluorocarbon elastomer, polyether polyurethane, etc. Examples of hydrophilic fibers, include but should not be limited to the following: polyester polyurethane, polyester elastomer Arnitel brand from Akzo Chemical), poly(styrene-co-butadiene) and poly(ethylene-propylene-diene).

The increase in weight of the tubing by the added fibers may range from 10% to 80% by weight, depending upon the number of passes of elastomeric polymer fibers. The tubing is then removed from the mandril and allowed to dry.

As illustrated in FIG. 1, a typical process for producing a multi-layer poly(tetrafluoroethylene)/elastomer implant is described as follows:

Step 1—Blending: A lubricated poly(tetrafluoroethylene) powder and lubricated poly(tetrafluoroethylene)/-elastomer powder mixture are prepared. From about 12 to about 25% mineral oil may be added to the poly(tetrafluoroethylene) powder to add lubricity. The elastomer may be selected from the group consisting of polyvinylidene fluoride co-hexafluoropropylene, poly(tetrafluoroethylene-co-perfluoro(methylvinylether)), poly(tetrafluoroethylene-co-propylene), poly(vinylidene-co-chlorotrifluoroethylene), silicones, fluorosilicones, fluoroalkoxy phosphazenes, segmented copolyester ether, styrene butadiene block copolymers, polyethers, acrylonitrile butadienes, isoprenes, polyurethanes and mixtures thereof. Preferred elastomers are silicones and poly(tetrafluoroethylene-co-propylene) sold under the trade name Aflas, manufactured by the Asahi Glass Company. Both are high temperature resistant elastomers. The elastomer is mixed with Freon TF to form a solution. From about 2 to about 10% elastomer is added to the solution. Further, the mineral oil lubricant is added to the solution in amounts ranging from about 5 to about 20% by weight. Further, the elastomer solution is added or sprayed upon a second amount of poly(tetrafluoroethylene) powder. From about 5 to about 50% of the elastomer by weight of the poly(tetrafluoroethylene) is added in solution to the poly(tetrafluoroethylene) powder. Both the lubricated poly(tetrafluoroethylene) powder and the poly(tetrafluoroethylene) powder wetted with the elastomer are mixed by tumbling in separate steps. A catalyst such as benzoyl peroxide may be added to provide elasticity and durability to the final product via crosslinking the elastomer portion. The catalyst is added in amounts ranging from about 0.01 to about 0.5% by weight of the poly(tetrafluoroethylene).

Step 2—Preforming: To manufacture tubing, a preferred embodiment of the present invention, a concentric tube is inserted inside the pre-former to divide the pre-former into two concentric spaces. The lubricated poly(tetrafluoroethylene) powder is loaded into the inner space while the lubricated poly(tetrafluoroethylene) powder/elastomer mixture is loaded into the outer space of the pre-former as shown in FIG. 1. In this application, the extrudate would have a relatively thin luminal layer of poly(tetrafluoroethylene) alone, having distinct fibril nodal microstructure for excellent blood contact as well as having luminal hydrophobicity for desired water entry pressure. The outer layer of poly(tetrafluoroethylene)/elastomer provides elasticity to improve compliance and as a transitional matrix to provide desired bonding between the inner and very outer layers. The powders are compressed to 50 to about 100 psi to form a dual layer pre-form or billet.

Step 3—Extrusion: The asymmetric pre-form is placed in an extruder which under hydraulic pressure forces the composite structure out of the die. Th extrudate is thin walled and flexible and not too rigid.

Step 4—Curing: The elastomer portion of th extrudate may optionally then be cured at a temperature of about 150° F. to 350° F. for about 2 hours.

Step 5—Expansion: The extrudate is dried to evaporate the lubricant. Generally, the tubing is heated within a temperature range of about 35° C. to about 327° C., preferably to about 300° C. which is below the crystalline melting point of poly(tetrafluoroethylene) and expanded at a rate of about 5% per second to about 100% per second so that the final length is about 150 to about 600, preferably about 350% of the original length. Further, the tubing is sintered by being placed in a preheated oven at a temperature ranging from 342° C. to 390° C. for a relatively short period of time.

Step 6—Radial Expansion: The expanded sintered tubing is radially expanded by placement of the tubing over a tip-tapered mandril, as described in co-pending application Ser. No. 935,237. The inside diameter of the tubing, which is normally about 4 mm to about 8 mm, is radially expanded to be about 6 mm to about 10 mm. In this step, the poly(tetrafluoroethylene) fibril-nodes are relaxed in the radial direction so that the elastomer solely can contribute to the radial compliance. This radial expansion step may take place before or after the sintering of the tubing and to some degree, effects the asymmetry of the pores in the layers. The process may end at this point wherein the product exhibits excellent porosity, compliance, strength, elasticity, luminal hydrophobicity and biocompatibility. It is suitable for in vivo implantation and provided for good tissue ingrowth. For an improvement in various properties, the process may be continued to produce additional multi-layered products.

Step 7—Elastomer Impregnation: (Formation of the optional elastomeric polymer coating layer). The tubing is dipped into a solution of elastomer so that the outer surface develops a layer of the elastomer as the third layer or possibly outer layer. The elastomer is porous to promote periprosthetic tissue ingrowth. In an elastomer solution containing about 5% by weight elastomer, and a solvent such as 1,1,1-trichloroethane in amounts ranging from about 1 to about 10% by weight of the solution, the tubing should be immersed for about 1 to about 10 minutes. It is not desired to have the elastomer permeate the poly(tetrafluoroethylene)/elastomer layer and migrate into the lumen. Alternatively, the elastomer solution may be sprayed on the poly(tetrafluoroethylene)/elastomer layer. The elastomer solution may optionally contain therapeutic agents including but not limited to antibiotic and/or hemostatic substances.

Step 8—Winding: (Formation of the optional elastomeric polymer fiber layer) A catalyst may optionally be added to the elastomer solution to aid in the curing. An elastomer solution or melt is pushed under pressure through a fine orifice forming a fiber. The orifice moves with respect to a rotating mandril. The fiber is thus wrapped on the mandril. However, the winding may be accomplished with a conventional apparatus when the fiber is wound around the tubing which is placed on a mandril. The angle of winding should be about 10 to about 85 degrees. The elastomeric polymer fiber wound around the tubing should form a porous nonwoven network because it is usually heated or containing a conventional solvent to promote fiber-fiber bonding when the fibers reach the mandril. Preferably, an elastomer is sprayed onto the fibers being wound on the mandril to promote fiber bonding. Typically, the fiber diameter may be from about 10 to about 200 microns, preferably about 20 to about 50 microns. Preferably, the fibers are poly(tetrafluoroethylene-co-porpylene) or silicone or polyurethane or segmented copolyester ether or mixtures thereof. The winding angle for applying the fibers to the mandril may vary from about 10 to about 85 degrees, preferably from about 30 to about 75 degrees. The fibers may contain catalyst to aid in curing as conventionally known in the art. The nonwoven fiber network is porous and may contain pore structures different from the fibrilnodal microstructure seen in the other layers. The compliance of the tubing can be maintained by determining the amount of the elastomer added to the final product in relation to the weight of the poly(tetrafluoroethylene). Preferred ratios are about 5 to about 120%.

Step 9—Curing: Curing occurs at a temperature of about 150° to about 350° F. The product is then ready for cutting.

In an alternate embodiment, silicone elastomer and silicone fluid may be premixed with the poly(tetrafluoroethylene) powder and subjected to the aforementioned process. The silicone elastomer and the silicone fluid effects the final poly(tetrafluoroethylene) fibrilnodal micropores. The silicone fluid is not generally a lubricating oil, and should not be treated as such. In the composition, mineral oil should still be used as lubricant. The silicone fluid is removed from the composite structures during the high temperature expansion or sintering step. To produce a silicone fluid-free poly(tetrafluoroethylene)/elastomer product, ultrasonic leaching in 1,1,1-trichloroethane or Freon may be incorporated into the process.

Expansion of about 250%, as shown in the above-described process, will produce an internodal distance of the luminal poly(tetrafluoroethylene) layer of about 20 to about 30 microns. The second layer of the composite structure, containing the mixture of poly(tetrafluoroethylene) powder and elastomer dispersion, for example, silicone, plus the addition of the silicone fluid, which when evaporated would generate an internodal distance within the poly(tetrafluoroethylene)/elastomer intermediate layer of from 30 to about 500 microns, preferably about 50 to about 100 microns. The internodal distance shown in the second layer is excellent for fibroblast tissue ingrowth, rather than undesired encapsulation, as healing progresses.

The above prepared the composite structure may then dipped in, or sprayed with an elastomer to form an outer elastomeric polymer layer. Next the elastomeric polymer fibers may be wrapped about the composite structure. The fibers are spirally wound on the tubing to form a non-woven fibrous matrix with the pore size of about 100 to about 2000 microns, preferably about 200 to about 500 microns. The large pore size and high porosity provides an excellent site for periprosthetic tissue anchoring. This is an improvement over an outer surface of poly(tetrafluoroethylene) which promotes little, if any tissue ingrowth and has little bonding strength. In this embodiment, each layer has a different pore size, pore shape and porosity, all of which promotes tissue growth and tissue anchoring.

An alternate embodiment comprises a luminal layer of poly(tetrafluoroethylene)/elastomer and a second layer of poly(tetrafluoroethylene). This combination of layers provides for better hydrophilicity due to the elastomer in the luminal layer. Subsequently, the previously described elastomer coating and elastomeric polymer fiber layers may be optionally added.

Figure 2:
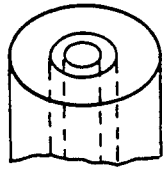
FIG. 2 is a schematic cross-sectional view of an implantable vascular graft in accordance with an embodiment of the present invention.

FIG. 2 shows an embodiment of the present invention having a luminal poly(tetrafluoroethylene) layer and poly(tetrafluoroethylene)/elastomer outer layer.

Figure 6:
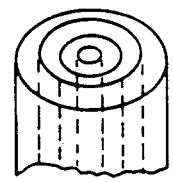
FIG. 6 is a schematic cross-sectional view of an implantable vascular graft in accordance with a still further embodiment of the present invention.

FIG. 6 shows an embodiment of the present invention having the layers shown in FIG. 2 as well as an optional outer layer of elastomeric polymer fibers.

The following examples describe the processes and products within this invention as well as a further description of the properties of the porous tetrafluoroethylene polymers/elastomers. As indicated above, some of the properties of these porous mixtures are substantially different from the corresponding properties of conventionally extruded or molded tetrafluoroethylene polymers. As a result of these differences, the porous composite structure is useful in many applications involving medical implants and vascular grafts.

EXAMPLE 1

This example describes the process of manufacturing a radially-asymmetric poly(tetrafluoroethylene)-elastomer composite vascular graft that consists of three concentric layers: poly(tetrafluoroethylene)-elastomer luminal layer, poly(tetrafluoroethylene)-elastomer intermediate layer, and an elastomer fibrous outer layer. Elastomers such as Aflas elastomer, a copolymer of tetrafluoroethylene and propylene, manufactured by the Asahi Glass Company, can be used in the asymmetric composite structure.

During the preforming stage, polytetrafluoroethylene powder sold under the trade name Fluon CD123 and manufactured by ICI Americas, was lubricated with about 20% by weight on the final solid basis by mineral spirits. The poly(tetrafluoroethylene) powder was loaded into the inner concentric layer while a blend of lubricated 95% poly(tetrafluoroethylene) - 5% Aflas elastomer mixture was loaded into the outer concentric layer. The divider in the preformer was thereafter removed without disturbing the layered powders. The asymmetric billet was extruded under conditions of temperatures about 90° F. and pressure 500 psi to form extrudates having an internal diameter of 4 mm.

The extrudates were expanded 300% at an expansion rate of about 10% per second in an oven, at a temperature of 500° F. followed by flash sintering at a temperature of 700° F. for a time period of 5 minutes. The sintered asymmetric poly(tetrafluoroethylene)-Aflas extrudate or graft had a wall thickness of about 0.48 mm. and was coded 1A. The sintered graft was then radially enlarged from 4 mm. to 5 mm. inside diameter and impregnated with an Aflas elastomer solution in accordance with the procedures shown in co-pending patent application Serial No. 935,237. The weight gain due to the addition of the elastomer during impregnation was 16% by weight. This graft was coded 1B.

Graft 1B was loaded on a mandril. Aflas elastomeric polymer fibers were then wound and bonded onto the poly(tetrafluoroethylene)-Aflas porous graft. The winding angle ranged from 10° to 80° with respect to the axial direction. The weight gain as a result of the Aflas elastomeric polymer fibers winding range from 30% to 80% depending upon the number of passes of Aflas fibers. The finished poly(tetrafluoroethylene)-elastomer composite graft was coded 1C. This manufacturing procedure follows the process shown in FIG. 1.

Both grafts 1A and commercially available Gore-Tex vascular graft, which served as a control, showed a compliance of less than $1.0 \times 10-2\%$/mmHg. For reference, a human femoral artery generally has compliance, based on outside diameter measurement, of $5.9 \times 10-2\%$/mmHg. As a result of post processing procedures, that is, radial enlargement and elastomer impregnation, graft 1B showed an improved compliance at $1.9 \times 10-2\%$/mmHg. The radially asymmetric poly(tetrafluoroethylene)-elastomer composite graft 1C exhibited a compliance range from 2.5 to $5.2 \times 10-2\%$/mmHg, depending on how many passes of elastic fibers had been wound at a particular winding angle. In general, the high-angle winding provided radial tensile strength, kink resistance, suture retention strength, and aneurysm protection, whereas the low-angle winding provided longitudinal tensile strength and radial compliance.

The suture retention strength was measured for grafts 1A and 1C. Graft 1A maintained a high suture retention strength of 416 grams while the suture retention strength of the poly(tetrafluoroethylene)-elastomer composite graft 1C showed a strength of 535 grams.

EXAMPLE 2

This example describes a process of manufacturing a radially-asymmetric vascular graft without outside fiber winding. A billet was prepared by loading about ⅔ of a lubricated poly(tetrafluoroethylene) powder into the outer concentric layer and about ⅓ of the lubricated mixture of 0% poly(tetrafluoroethylene) and 20% silicone elastomer was produced by diluting the silicone dispersion Q7-2213 from Dow Corning in 1,1,1-trichloroethane solvent. The 6 mm. inside diameter extrudate was cured with respect to silicone at 50° C. overnight. The cured extradate was expanded and sintered. It was coded 2A.

Figure 3:
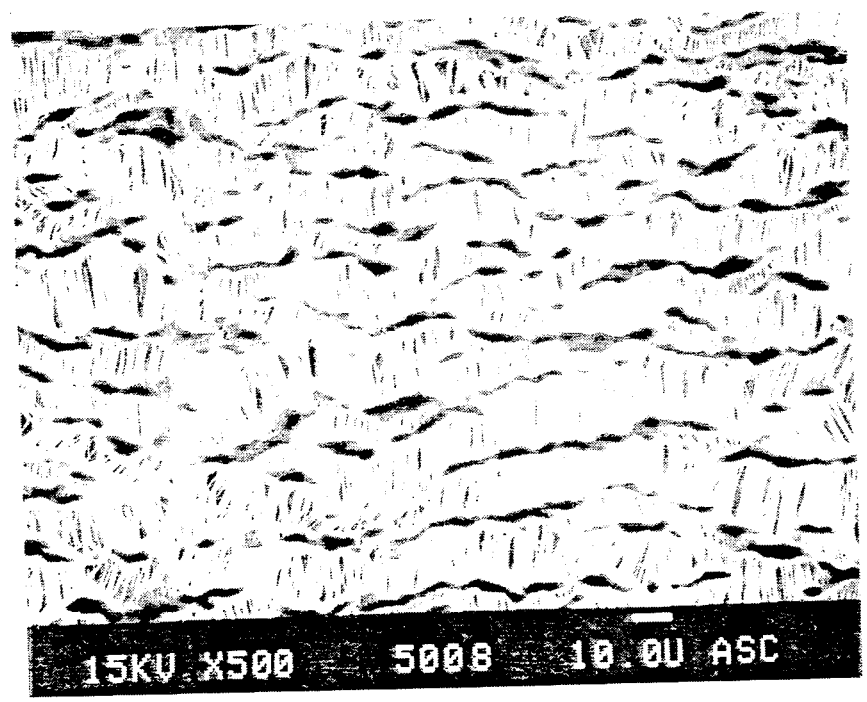
FIG. 3 depicts a microphotograph of a through section of an embodiment of an implantable vascular graft

Sample 2A exhibits very typical fibril-nodal microstructure. The lumen surface was very smooth for the pre-cured graft. Another similar extrudate without curing was expanded and sintered. The lumen surface was very rough, probably due to the instability of uncured silicone when the extrudate was exposed to sudden high temperature. FIG. 3 shows the SEM lumen which consists of 80% poly(tetrafluoroethylene) and 20% silicone. Since silicone does not form the fibril-nodal structure as poly(tetrafluoroethylene) does, the silicone probably functions as a coating on the surface of the poly(tetrafluoroethylene) fibril-nodes.

A conventional water-entry pressure test was performed on Sample 2A. The water-entry pressure was 10.8 psi which is exceedingly high. A comparable poly(tetrafluoroethylene) or homogeneous poly(tetrafluoroethylene)/elastomer graft with similar porosity would have a water-entry pressure of about 4–5 psi as a result of the poly(tetrafluoroethylene) hydrophobicity. This high-water entry pressure may conceivably be due to the self-sealing effect of silicone in a radially-asymmetric poly(tetrafluoroethylene) silicone composite graft. The self-sealing mechanism is desirable for a vascular access device such as an A-V fistula for hemodialysis purposes. It is speculated that silicone may seal the needle puncture of a poly(tetrafluoroethylene)-type device when silicone is sandwiched between layers of poly(tetrafluoroethylene). The porosity of Sample 2A was 66%.

EXAMPLE 3

A thin-wall 95% poly(tetrafluoroethylene)/5% Aflas elastomer tubing was prepared by following the manufacturing process of co-pending application serial no 892,271 incorporated herein by reference. In this example, fibrous elastomer was wound onto the poly(tetrafluoroethylene)/elastomer composite graft. During post-processing, the expanded/sintered poly(tetrafluoroethylene)/elastomer tubing was placed onto a mandril and secured in a winder. The spraying-and-winding technique consists of winding an elastomeric polymer fibers onto the tubing and spraying elastomer solution simultaneously to bond the fibers. This technique was utilized to firmly bond the outside fibers onto the poly(tetrafluoroethylene)/elastomer tubing. The composite graft consists of polyurethane fibers (300 passes at 65° winding angle with respect to the axial direction, the fibers diameter being about 50 microns) winding and Aflas elastomer solution spraying intermittently. The sample was coded 3A.

The 4 mm inside diameter graft of Sample 3A was very soft and flexible with good suture retention strength and suturability. The graft was sterilized with ethylene oxide and used to replace a 4 cm portion of a canine femoral artery. The graft showed an in vivo compliance of about $5 \times 10-2\%$/mmHg by using an electromagnetic rheoangiometry system. This measurement system is described in an article by S. Klein "Effect of Suture Technique on Arterial Anastomotic Compliance" Arch Surg. 117;45–47 (1982). The in vivo compliance of said compliant graft sample 3A compares favorably with that from the adjacent femoral artery of the same canine.

EXAMPLE 4

The process of Example 3 was followed except that during post-processing, the expanded/sintered poly(tetrafluoroethylene)/elastomer tubing was dip coated into the Aflas elastomer prior to fiber winding, rather than spraying the elastomer as in Example 3, and winding 375 passes of polyurethane fibers in comparison to 300 passes in Example 3. The 4 mm radially asymmetric poly(tetrafluoroethylene)/elastomer composite graft was coded 4A.

The graft was very soft and flexible with good suture retention strength of 248 grams. It had a burst strength of greater than 90 psi which is higher than a typical poly(tetrafluoroethylene) type vascular grafts. The outer elastomeric polymer fibers reinforce the graft. The longitudinal tensile strength for said graft was higher than 4000 psi whereas its radial tensile strength was more than 400 psi.

The graft exhibited an in vivo compliance of about $4 \times 10-2\%$/mmHg by using the electromagnetic rheoangiometry system. The lower compliance as compared to Sample 3A in Example 3 was due probably to more fibers used in this graft 4A. In either case, the in vivo compliance was much higher than the control composite structure, a Gore-Tex graft which is about 0.9×10-2%/mmHg.

EXAMPLE 5

The T-Peel Test

The objective of the T-peel test is to determine the relative peel resistance of an adhesive bond between two flexible adherents. The peel strength test involves a stripping of a flexible member of an assembly that has been bonded with an adhesive to another member that may be flexible or rigid. The T-peel test is described in ASTM Method D-1876. For present purposes the T-peel test was modified.

The specimens were Samples 4A taken from Example 4. The specimens were 0.5" wide and 1" long and bonded over 1/2" of their length. The test was performed on a standard tensile testing machine, manufactured by Precision Instrument, Inc., at a linear speed of 0.09" per second. The specimen showed a peeling strength of 296 grams. This bonding strength between the poly(tetrafluoroethylene) elastomer tubing and outer elastomeric polymer fibers was strong enough to hold the composite graft without delamination. Thus it appears, that the spraying-and-winding technique to bond the outer elastomeric polymer fibers onto the poly(tetrafluoroethylene)/elastomer tubing is adequate.

EXAMPLE 6

Dip-coating or spray-coating of elastomer onto the poly(tetrafluoroethylene) elastomer tubing was employed with the radially-asymmetric poly(tetrafluoroethylene)/elastomer composite graft and similar results were obtained. The poly(tetrafluoroethylene)/elastomer composite graft was dipped into Aflas elastomer, silicone elastomer, and Cardiothane 51, a copolymer of polyurethane and silicone manufactured by Kontron, Inc. The tubing was dip-coated into 3.5 weight % solutions of the elastomers. The compliance improvement of the thin-walled (0.2 mm) 95% poly(tetrafluoroethylene)/5% elastomer tubing is shown in the following table. The control sample was the same tubing without dip-coating.

| Elastomer Coating | Coating Thickness, mm | Compliance × 10 - 2%/mmHg |
| --- | --- | --- |
| Control | 0 | 1.3 |
| Aflas | 0.08 | 1.5 |
| Silicone | 0.13 | 1.7 |
| Cardiothane 51 | 0.05 | 1.8 |

In order to increase the distance between the fibril-nodal micropores and therefore its pore size, silicone compatible fluid may be added and then removed from the poly(tetrafluoroethylene). This embodiment is shown in the following examples.

EXAMPLE 7

A mixture of 95% poly(tetrafluoroethylene), sold under the trade name Fluon CD-123 manufactured by ICI Americas and 5% by weight silicone sold under the trade name Q7-2213 manufactured by Dow Corning was prepared by adding 20% silicone fluid on a solid basis and tumbling for 1 hour. The silicone fluid is sold under the trade name 360 Medical Fluid manufactured by Dow Corning and has a 20 cs viscosity. The silicone fluid is a clear, colorless polydimethylsiloxane fluid. The mixture was loaded into the outer concentric layer of a pre-former. The inner concentric layer was loaded with poly(tetrafluoroethylene) powder lubricated with 20% by weight mineral spirit. The radially asymmetric powder was then compressed to 300 to 500 psi, and a solid billet was formed. The billet was placed in an extruder which, by hydraulic pressure, forces the mixture through an orifice. The extruded composite structure was cut into sections having a length of approximately 5 in. and an inside diameter of 6 mm. The sections were loaded onto a rack in an expansion oven. They were cured for 2 hours at 150° F. and then overnight at 300° F. The sections were thereafter expanded to 20 inches at an expansion rate of about 10% per second while at an expansion temperature of about 500° F. The samples were sintered at 680° F. and coded 7-X. The last digit "X" indicates the sintering time in minutes.

EXAMPLE 8

Theoretically, the evaporation of a silicone fluid from a cured silicone elastomer matrix generates the unexpected large pores with long internodal distances in a poly(tetrafluoroethylene)/silicone composite. To determine the residual content of leachable silicone, which presumably includes the silicone fluid and/or silicone oligomers out of the silicone elastomer, the sintered poly(tetrafluoroethylene)/elastomer/silicone products were left in an ultrasonic cleaner, manufactured by Branson Instrument Co., filled with 1,1,1-trichloroethane. After 30 minutes leaching, the weight losses on sintered products with different sintering times are shown in the following table.

| Sample Code | Sintering Time | Weight Loss After Leaching |
| --- | --- | --- |
| 7-1 | 1 min. | 5.3% |
| 7-3 | 3 | 3.8 |
| 7-5 | 5 | 3.2 |
| 7-10 | 10 | 2.7 |
| 7-15 | 15 | 1.8 |
| 7-0 | 0 | 12.9 as control |

Apparently, most of the silicone fluid is removed during the high temperature expansion or sintering step.

EXAMPLE 9

Figure 4A:
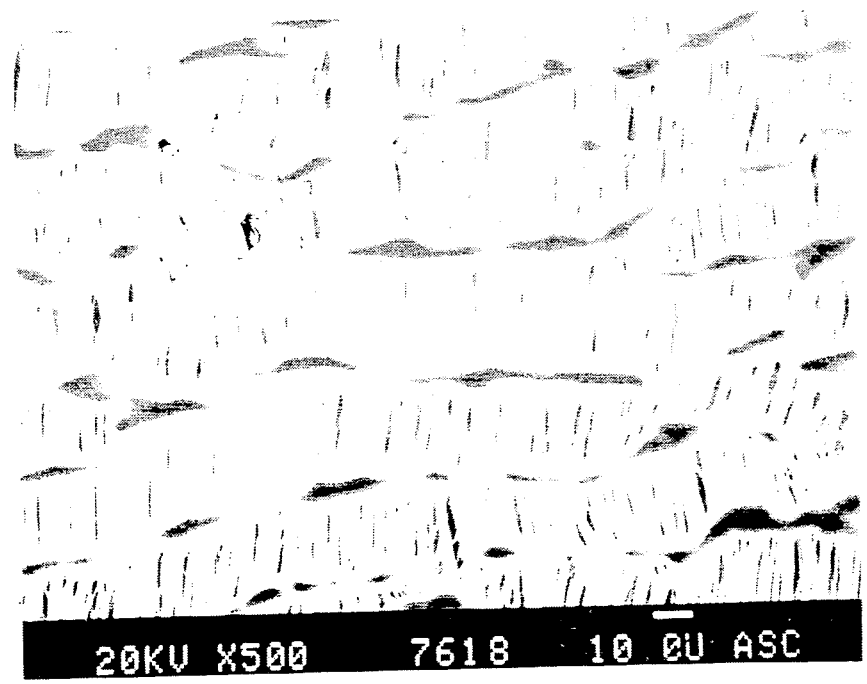
FIG. 4a depicts a microphotograph of a through section of an embodiment of an implantable vascular graft
Figure 4B:
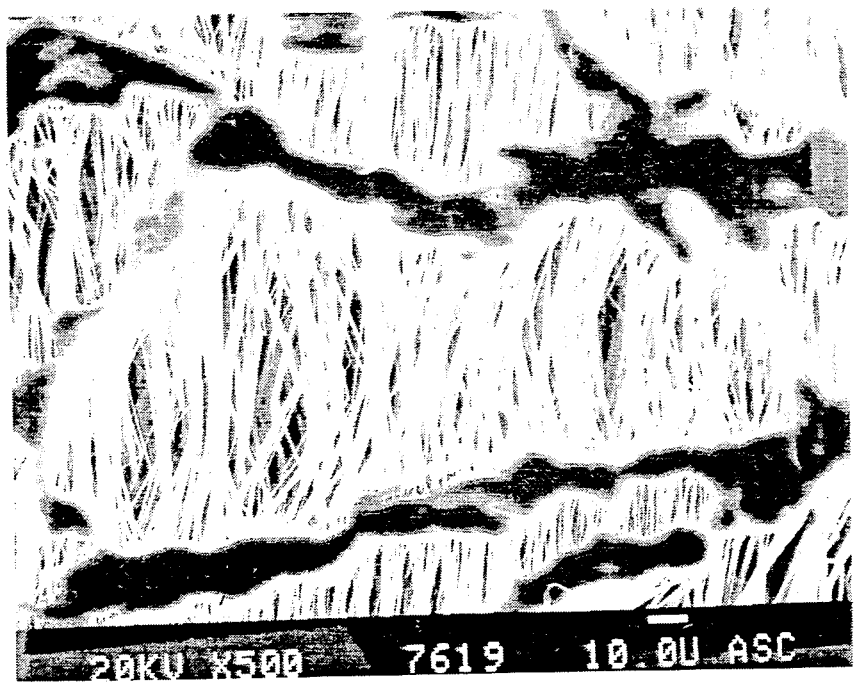
FIG. 4b depicts a microphotograph of a through section of an embodiment of an implantable vascular graft
Figure 4C:
FIG. 4c depicts a microphotograph of a through section of an embodiment of an implantable vascular graft.

Samples 7-3 (3 min. sintering) and 7-15 (15 min. sintering) were examined with scanning electron microscopy. FIGS. 4A and 4B show the lumen surface and exterior surface of Sample 7-3. Both surfaces indicate typical poly(tetrafluoroethylene) fibril-nodal microstructure. The internodal distance of the lumen surface is measured at about 25 microns where the internodal distance of the exterior surface is about 60 microns. The cross-section scanning electron microscopy as shown in FIG. 4C for sample 7-3 clearly demonstrates that the outer layer has as much larger pores than the inner layer as a result of the instant innovative process.

Figure 4D:
FIG. 4d depicts a microphotograph of a through section of an embodiment of an implantable vascular graft
Figure 4E:
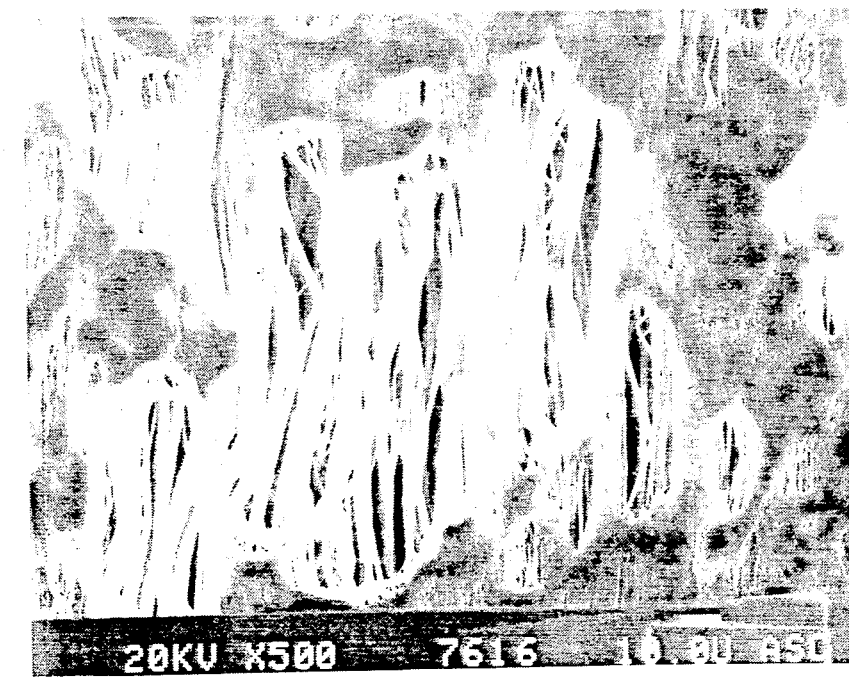
FIG. 4e depicts a microphotograph of a through section of an embodiment of an implantable vascular graft
Figure 4F:
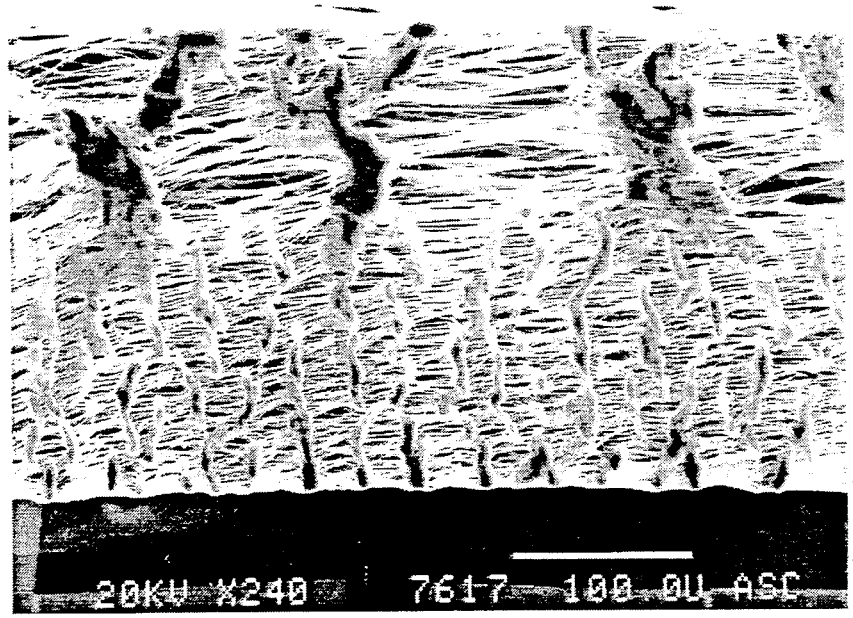
FIG. 4f depicts a microphotograph of a through section of an implantable vascular graft

Similarly, a poly(tetrafluoroethylene)/elastomer/silicone sample which had been sintered at 680° F. for 15 minutes, Sample 7-15, showed asymmetric pore sizes. FIGS. 4D and 4E show the lumen surface and exterior surface for Sample 7-15. The internodal distance of said lumen surface is measured at about 25 microns where that of the exterior surfaces is about 90 microns. The cross-sectional scanning electron microscopy as shown in FIG. 4F for sample 7-15 confirms the distribution of the asymmetric pore sizes.

EXAMPLE 10

Figure 5A:
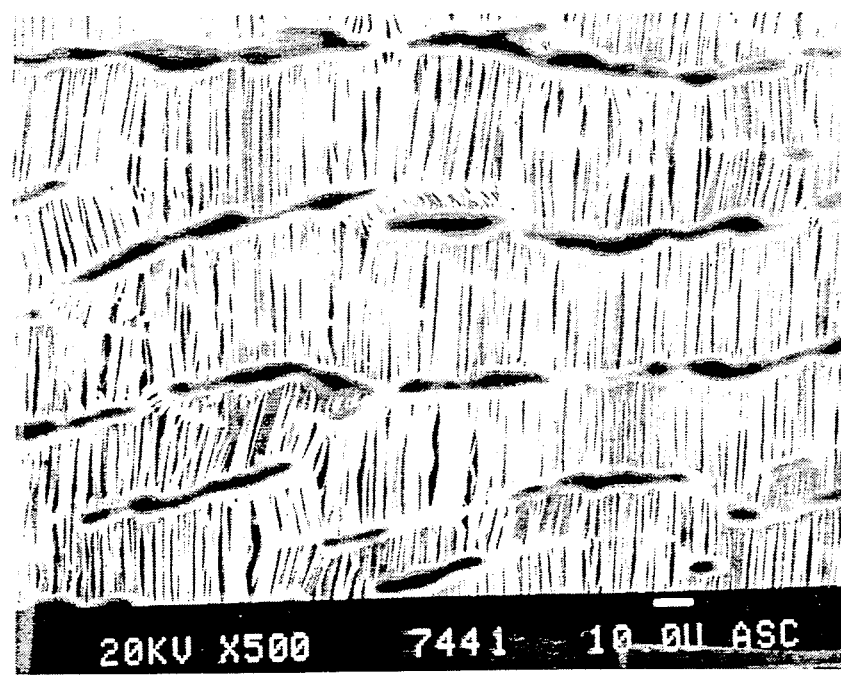
FIG. 5a depicts a microphotograph of a through section of an embodiment of an implantable vascular graft
Figure 5B:
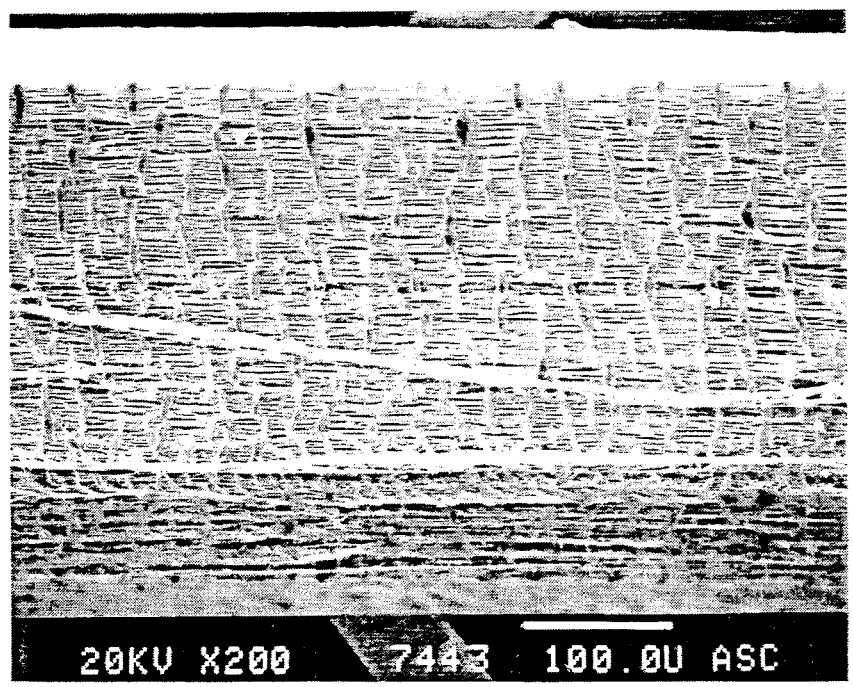
FIG. 5b depicts a microphotograph of a through section of an embodiment of an implantable vascular graft
Figure 5C:
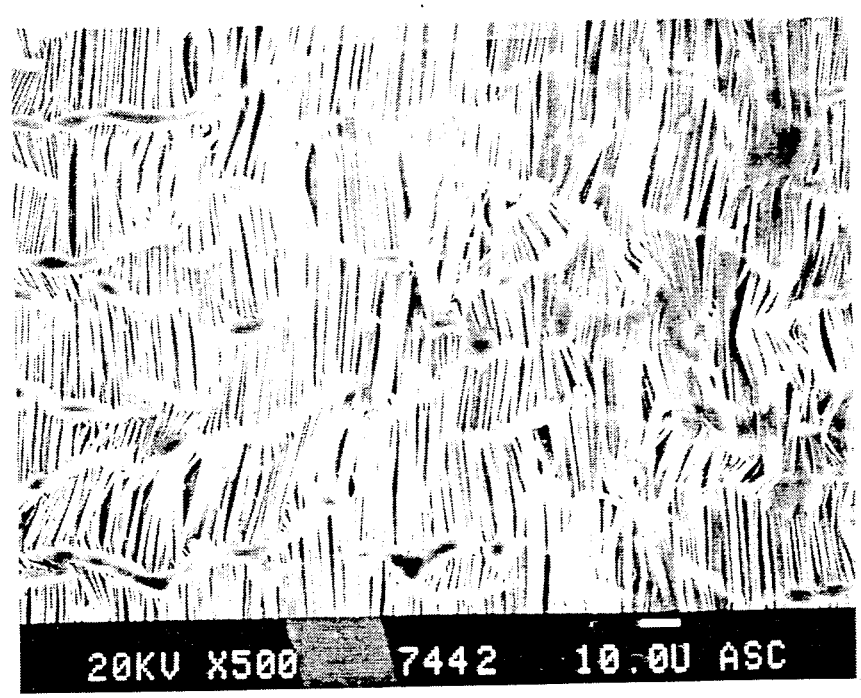
FIG. 5c depicts a microphotograph of a through section of an embodiment of an implantable vascular graft

For our comparison purposes, an asymmetric poly(tetrafluoroethylene)/silicone product following the procedure of Example 6 was formulated, except that mineral oil, instead of silicone fluid, was used in both the poly(tetrafluoroethylene) and poly(tetrafluoroethylene)/silicone layers. The product was fabricated and coded as Sample 10. This sample, containing poly(tetrafluoroethylene) and 5% silicone was examined under scanning electron microscopy. FIGS. 5A and 5B show the lumen surface and exterior surface of Sample 10. Both indicate very typical poly(tetrafluoroethylene) fibral-nodal microstructures. The internodal distance is constant from the lumen side through to the exterior side as shown in a crosssectional scanning electron microscopy, FIG. 5C. The lumen is at the lower side of the figure. The internodal distance was measured at about 25 microns. No asymmetric pore sizes were observed.

EXAMPLE 11

A poly(tetrafluoroethylene)/elastomer product with asymmetric pore sizes in a sandwich type configuration was fabricated. The lubricated poly(tetrafluoroethylene)/silicone powder with silicone fluid is loaded into the middle zone of a preformer. The adjacent zones are filled with a lubricated poly(tetrafluoroethylene) powder. The same process as described in Example 6 may be followed, preforming, extrusion, curing, expansion and sintering, to produce a poly(tetrafluoroethylene)/elastomer product with many large pores in the middle layer. The asymmetric large pores serve as a reservoir for elastomer deposition to produce an elastic poly(tetrafluoroethylene) product.

In accordance with another preferred embodiment, the elastomeric polymer fibers are applied to the composite structure while under tension. Specifically, the composite structure is in the shape of a tubular structure for use as a vascular graft. The tubular structure may include a luminal layer of polytetrafluoroethylene, with an outer layer of the polytetrafluoroethylene-elastomer blend. The structure may or may not include an outer elastomeric polymer coating. However, this embodiment may also include only a single layer of polytetrafluoroethylene, or a single layer of polytetrafluoroethylene-elastomer blend. The important aspect of this embodiment is the winding of the elastomeric polymer fiber under tension.

Those aspects of this embodiment pertaining to the composition and method of forming the polytetrafluoroethylene layer, polytetrafluoroethylene-elastomer blend layer, elastomeric coating, and the other aspects of the embodiments discussed previously are the same for this embodiment. That is, the manner of forming the composite structure having a layer of polytetrafluoroethylene and a layer of polytetrafluoroethylene-elastomer blend is as described above. However, in this embodiment, the composite structure need only have a single layer of either the polytetrafluoroethylene or the polytetrafluoroethylene-elastomer blend. Furthermore, there is no need to coat the resulting the composite structure with an elastomeric polymer as described above.

Furthermore, the types of elastomers useful for preparing the elastomeric polymer coating and the polytetrafluoroethylene-elastomer blend are the same for this embodiment. Accordingly, those aspects of this embodiment which are the same as described above will not be discussed after further herein.

As stated, this embodiment of the invention involves the application under tension of an elastomeric polymer fiber the composite structure. The fiber is released from the applied tension after being provided about the composite structure. This release allows the fiber to retract to its initial position. That is, the fiber is originally stretched by the application of tension, which when removed allows the fiber to retract because of its inherent elasticity. As the fiber retracts, the composite structure, or more precisely the vascular graft retracts. This reduces the original length, and width of the vascular graft. This reduction, or retraction of the vascular graft provides an inherent elasticity to the resulting graft.

The higher the percentage of retraction of the vascular graft, the more inherent elasticity is provided to the vascular graft. This retraction percentage is determined by the following formula:

$$\text{RETRACTION} = 1 - \frac{\text{ORIGINAL LENGTH} - \text{RETRACTED LENGTH}}{\text{RETRACTED LENGTH}}$$

The larger the percentage of retraction the greater the inherent elasticity. Preferably this percentage of retraction is from about 1 to about 50%, even more preferably from about 5 to about 30 %.

The percent of retraction is a function not only of the amount of tension applied to the elastomeric fibers, but also the angle at which the fibers are wound onto the vascular graft outer surface, and the number of windings of fiber about the given portion of the vascular graft.

The amount of tension applied to the fiber may range from about 5 to about 50 grams of weight applied to the fiber during the winding process. The actual amount of tension applied to the fibers, as measured by a Digital Gram Gauge Model DFG2 Dynamometer manufactured by Chatillon, is dependent upon the material from which the fibers are prepared, the number of windings and the type of polytetrafluoroethylene used to prepare the vascular graft.

The winding angle is that angle measured with respect to the center line of the vascular graft. The smaller the angle the greater the percent of retraction. Thus the desired percent of retraction may be achieved by varying the winding angle from about 30° to about 80°, more preferably from about 30° to 70°.

The number of windings per centimeter may vary from about 2 to about 20, with the preferred number being from about 4 to about 10. The greater the number of windings the greater the percent of retraction and thus intrinsic elasticity.

In accordance with a more preferred version of this embodiment, the percent of retraction is varied along the length of the vascular graft. That is, either one or more of the winding angle, tension, or number of windings may be altered as the fiber is being wound about the vascular graft to provide for differing degrees of retraction along the length of the vascular graft. Preferably the winding angle, number of windings and/or applied tension are controlled to provide that the percent of retraction is greatest along the ends of the vascular graft. This is particular beneficial since the ends of the vascular graft receive the greatest amount of stress. That is, the vascular graft bends most at its ends during the alternating systolic and diastolic cycles. The increased percent of retraction at the vascular graft ends provides a greater degree of intrinsic elasticity. Thus the ends can absorb a greater degree of stress or bending. Furthermore, the amount of windings applied to the respective ends may be increased in order to enhance the percent of retraction. That is, a greater number of fibers applied under tension will increase the percent of retraction.

The number of fiber windings also effects the porosity of the final product. A greater number of fiber windings reduces the porosity. Thus in accordance with the more preferred embodiment, the number of fiber windings is greatest at that portion of the vascular graft adjacent to the graft ends, with the number of fiber windings being less along the mid portion of the graft. This provides not only a greater percent of retraction along the ends, but a lesser porosity. The greater porosity is present along the graft mid portion, which is more important for tissue ingrowth. Thus a vascular graft can be prepared which possess a desired degree of elasticity at its ends, while maintaining a desired degree of porosity along the mid portion.

Referring now to FIG. 7 and 8, schematic illustrations of a mechanism for applying the elastomeric fiber. As seen in FIG. 7, a schematic illustration of a mechanism for applying the elastomeric polymer fiber to the vascular graft is seen generally at 100. Mechanism 100 includes a first device 101 about which the fiber is loaded, and which is operable for controlling the application of tension to the fiber during the winding process. The mechanism 100 also includes three spools 103, 106 and 107 about which the train of fiber, seen generally at 102 is wound.

The spools 103, 106 and 107 are typically spring loaded so as to apply or maintain tension upon the fiber train 102. The device 101 for applying the tension may be any suitable apparatus which can be operated to apply such tension. For example, device 101 may be a computer controlled apparatus which pulls upon the fiber train 102 to apply the desired degree of tension.

The fiber train 102 is looped about the first spool 103, which is partially submerged in a solution bath, seen generally at 104. This solution bath contains an elastomer and a suitable solvent for the chosen elastomer. Preferably the chosen elastomer is silicone and the desired solvent is 1,1,1- trichloroethane, freon, or tetrahydrofuran. The concentration ratio of the solvent and the elastomer are usually from about two percent to about fifteen percent, on a solids basis.

The fiber train 102 is then looped about and spool 106 and 107 sequentially. A source for removing the solvent applied to the fiber train 102 in the first bath 103 is positioned adjacent to the spool 106, with the source being illustrated as an infrared source 105. The last spool 107 is also partially submerged in a solution bath, seen generally at 108, which contains a suitable solvent and an elastomer, i.e. silicone.

The now coated fiber train 102 is passed to an appropriate mechanism, seen in FIG. 8, for wrapping the fiber about a mandrel 109 upon which the vascular graft 113 is loaded.

As seen in FIG. 8, the vascular graft 113 is loaded onto the mandrel 109, which is coupled at both ends to a mechanism which is operable for rotating the mandrel 109, which mechanism is seen at 110. As also seen in FIG. 8, the fiber train 102 is wrapped about the vascular graft 113 at varying degrees of tension. A first region of low tension is seen at 111, with a region of higher tension seen generally at 113. As seen, the fiber in the higher tension region 111 are spaced further apart than the fibers in the region of lower tension 113. This is the result of the effect caused by the retraction of the vascular graft when the tension on the fiber is released.

While the above described embodiment utilizes a single fiber which is wound about the vascular graft, it is suitable to use more than one fiber for this purpose. In this regard, two or more individual fibers may be wound about the vascular graft, with such fibers being applied under the same or different tensions, winding angle and density.

While the invention has been described in detail and with reference to specific embodiments thereof, it will be apparent to one skilled in the art that various changes and modifications can be made therein without departing from the spirit and scope thereof.

We claim:

1. A vascular graft comprising a porous polytetrafluoroethylene tubing and elastic fibers wrapped about the external surface of said tubing, with said fibers being wrapped about said surface at varying angles and under varying degrees of applied tension to promote the retraction of said tubing from the original size of said polytetrafluoroethylene tubing without said wrapping of fibers, and wherein said elastic fibers are wrapped under higher degrees of tension at locations adjacent to said tubing opposite ends.

2. The vascular graft of claim 1 wherein said tubing is retracted from about one to about fifty percent of said tubing original size.

3. The vascular graft of claim 1 wherein said tubing is retracted from about five to about thirty percent of said tubing original size.

4. The vascular graft of claim 2 wherein said desired winding angle is from about thirty to about eight degrees.

5. The vascular graft of claim 3 wherein said desired winding angle is from about thirty to about eighty degrees.

6. A vascular graft comprising a porous polytetrafluoroethylene tubing and elastic fibers wrapped under varying degrees of tension about the external surface of said tubing, with said elastic fibers being wrapped under higher degrees of tension at locations adjacent to said tubing opposite ends.

* * * * *